United States Patent
Angell et al.

(10) Patent No.: US 7,166,623 B2
(45) Date of Patent: Jan. 23, 2007

(54) 2'-METHYL-5'-(1,3,4-OXADIAZOL-2-YL)-1,1'-BIPHENYL-4-CARBOXAMIDE DERIVATIVES AND THEIR USE AS P38 KINASE INHIBITORS

(75) Inventors: Richard Martyn Angell, London (GB); Paul Bamborough, Stevenage (GB); George Stuart Cockerill, London (GB); Kathryn Jane Smith, Stevenage (GB); Ann Louise Walker, Stevenage (GB)

(73) Assignee: Glaxo Group Limited, Greenford (GB)

( * ) Notice: Subject to any disclaimer, the term of this patent is extended or adjusted under 35 U.S.C. 154(b) by 71 days.

(21) Appl. No.: 10/492,497

(22) PCT Filed: Oct. 16, 2002

(86) PCT No.: PCT/EP02/11575

§ 371 (c)(1),
(2), (4) Date: Apr. 15, 2004

(87) PCT Pub. No.: WO03/032987

PCT Pub. Date: Apr. 24, 2003

(65) Prior Publication Data

US 2005/0090491 A1 Apr. 28, 2005

(30) Foreign Application Priority Data

Oct. 17, 2001 (GB) ................. 0124938.2

(51) Int. Cl.
*A01N 43/36* (2006.01)
*C07D 271/10* (2006.01)

(52) U.S. Cl. ........................ 514/364; 548/145
(58) Field of Classification Search ............... 548/143; 514/364
See application file for complete search history.

(56) References Cited

U.S. PATENT DOCUMENTS

| | | | |
|---|---|---|---|
| 4,200,750 A | 4/1980 | Warner, Jr. et al. | |
| 4,968,804 A | 11/1990 | Stanek et al. ............. | 546/257 |
| 5,064,832 A | 11/1991 | Stanek et al. ............. | 514/256 |
| 5,236,934 A | 8/1993 | VanAtten | |
| 5,246,943 A | 9/1993 | Blankley et al. | |
| 5,521,213 A | 5/1996 | Prasit et al. | |
| 5,534,518 A | 7/1996 | Henrie, II et al. | |
| 5,658,903 A | 8/1997 | Adams et al. | |
| 5,858,995 A | 1/1999 | Kawai et al. | |
| 5,877,190 A | 3/1999 | Dhainaut et al. ......... | 514/337 |
| 5,932,576 A | 8/1999 | Anantanarayan et al. | |
| 5,945,418 A | 8/1999 | Bemis et al. | |
| 5,977,103 A | 11/1999 | Adams et al. | |
| 6,060,491 A | 5/2000 | Pruitt et al. ............. | 514/355 |
| 6,080,767 A | 6/2000 | Klein et al. ............. | 514/357 |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,174,887 B1 | 1/2001 | Haruta et al. | |
| 6,251,914 B1 | 6/2001 | Adams et al. | |
| 6,277,989 B1 | 8/2001 | Chakravarty et al. | |
| 6,323,227 B1 | 11/2001 | Klein et al. ............. | 514/357 |
| 6,392,047 B1 | 5/2002 | Geissler et al. ......... | 546/260 |
| 6,399,627 B1 | 6/2002 | Song et al. ............. | 514/307 |
| 6,420,561 B1 | 7/2002 | Haruta et al. ........... | 544/399 |
| 6,436,925 B1 | 8/2002 | Lubisch et al. | |
| 6,448,257 B1 | 9/2002 | Mavunkel et al. ...... | 514/292 |
| 6,451,794 B1 | 9/2002 | Beswick et al. | |
| 6,498,166 B1 | 12/2002 | Campbell et al. | |
| 6,509,361 B1 | 1/2003 | Weier et al. | |

(Continued)

FOREIGN PATENT DOCUMENTS

DE    19817491    10/1999

(Continued)

OTHER PUBLICATIONS

Boehm et al., *Expert Opinion of Therapeutic Patents*, vol. 10 (1) pp. 25-37 (2000).
Boehm, et al, *Journal of Medicinal Chemistry*, vol. 39(20) pp. 3929-3937 (1996).

(Continued)

*Primary Examiner*—Joseph K. McKane
*Assistant Examiner*—Yong Chu
(74) *Attorney, Agent, or Firm*—Dara L. Dinner; Stephen Venetianer; Charles M. Kinzig

(57) ABSTRACT

Compounds of formula (I):

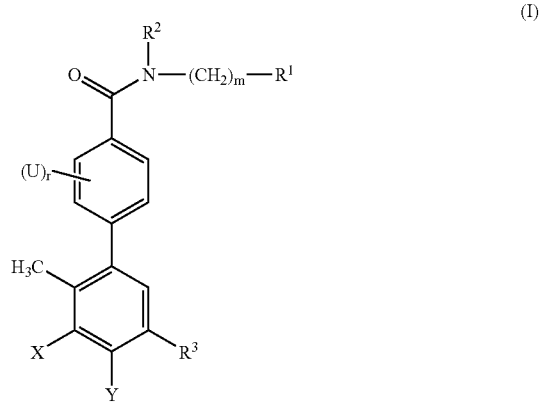

or pharmaceutically acceptable salts or solvates thereof, and their use as pharmaceuticals, particularly as p38 kinase inhibitors.

14 Claims, No Drawings

U.S. PATENT DOCUMENTS

| | | | |
|---|---|---|---|
| 6,509,363 B1 | 1/2003 | Salituro et al. | |
| 6,545,054 B1 | 4/2003 | Song et al. | 514/603 |
| 6,576,632 B1 | 6/2003 | Goldstein et al. | 514/242 |
| 6,579,872 B1 | 6/2003 | Brown et al. | |
| 6,605,625 B1 | 8/2003 | Peukert et al. | 514/333 |
| 6,638,980 B1 | 10/2003 | Su et al. | |
| 6,696,464 B1 | 2/2004 | McClure et al. | 514/303 |
| 6,699,994 B1 | 3/2004 | Babu et al. | 546/306 |
| 6,774,127 B1 | 8/2004 | Adams et al. | |
| 6,794,377 B1 | 9/2004 | Peukert et al. | 514/183 |
| 6,821,965 B1 | 11/2004 | Brown et al. | 514/217.05 |
| 6,855,719 B1 | 2/2005 | Thomas et al. | |
| 6,867,209 B1 | 3/2005 | Mavunkel et al. | 524/253 |
| 6,924,392 B1 | 8/2005 | Peukert et al. | 564/155 |
| 6,936,719 B1 | 8/2005 | Babu et al. | 546/323 |
| 6,956,037 B1 | 10/2005 | Brown et al. | 514/235.5 |
| 2001/0011135 A1 | 8/2001 | Reidl et al. | |
| 2003/0055088 A1 | 3/2003 | Shao et al. | 514/340 |
| 2003/0139605 A1 | 7/2003 | Riedl et al. | 546/291 |
| 2003/0225089 A1 | 12/2003 | Jung et al. | 514/242 |
| 2004/0038858 A1 | 2/2004 | Dorsch et al. | |
| 2004/0053942 A1 | 3/2004 | Alberti et al. | |
| 2004/0116479 A1 | 6/2004 | Haviv et al. | 514/356 |
| 2004/0128287 A1 | 7/2004 | Barth et al. | 514/419 |
| 2004/0162281 A1 | 8/2004 | Babu et al. | 514/217.03 |
| 2004/0176446 A1 | 9/2004 | Alonso-Alija et al. | |
| 2004/0242868 A1 | 12/2004 | Angell et al. | |
| 2004/0249161 A1 | 12/2004 | Angell et al. | |
| 2004/0254200 A1 | 12/2004 | Davis et al. | 514/260.1 |
| 2004/0266839 A1 | 12/2004 | Angell et al. | |
| 2004/0267012 A1 | 12/2004 | Angell et al. | |
| 2005/0020540 A1 | 1/2005 | Angell et al. | |
| 2005/0020590 A1 | 1/2005 | Lang et al. | 514/230.5 |
| 2005/0038014 A1 | 2/2005 | Angell et al. | |
| 2005/0065195 A1 | 3/2005 | Angell et al. | |
| 2005/0090491 A1 | 4/2005 | Angell et al. | 514/227.8 |
| 2005/0176964 A1 | 8/2005 | Aston et al. | 546/268.1 |

FOREIGN PATENT DOCUMENTS

| | | |
|---|---|---|
| DE | 10063008 | 6/2000 |
| DE | 10110749 | 9/2002 |
| EP | 0 533 266 | 9/1992 |
| EP | 0 533 268 | 9/1992 |
| EP | 0 849 256 | 6/1998 |
| EP | 0 346 841 | 6/2003 |
| EP | 0 430 033 | 4/2004 |
| GB | 2 276 161 | 3/1993 |
| GB | 2 276 162 | 3/1993 |
| GB | 2 273 930 | 12/1993 |
| GB | 2 295 387 | 5/1996 |
| JP | 11218884 | 8/1999 |
| WO | WO 94/15920 | 7/1994 |
| WO | WO 94/18980 | 9/1994 |
| WO | WO 95/11243 | 4/1995 |
| WO | WO 95/06636 | 5/1995 |
| WO | WO 95/06644 | 5/1995 |
| WO | WO 95/15954 | 6/1995 |
| WO | WO 95/17401 | 6/1995 |
| WO | WO 95/29904 | 11/1995 |
| WO | WO 95/29907 | 11/1995 |
| WO | WO 95/30675 | 11/1995 |
| WO | WO 96/06840 | 3/1996 |
| WO | WO 96/31508 | 10/1996 |
| WO | WO 96/31509 | 10/1996 |
| WO | WO 97/03034 | 1/1997 |
| WO | WO 98/56377 | 12/1998 |
| WO | WO 98/57934 | 12/1998 |
| WO | WO 99/12930 | 3/1999 |
| WO | 99/32463 | 7/1999 |
| WO | WO 99/58523 | 11/1999 |
| WO | WO 99/59959 | 11/1999 |
| WO | WO 00/12074 | 3/2000 |
| WO | WO 00/12497 | 3/2000 |
| WO | WO 00/17175 | 3/2000 |
| WO | WO 00/26216 | 5/2000 |
| WO | WO 00/41698 | 7/2000 |
| WO | WO 00/52008 | 9/2000 |
| WO | WO 00/56738 | 9/2000 |
| WO | WO 00/71493 | 11/2000 |
| WO | WO 00/71509 | 11/2000 |
| WO | WO 00/71510 | 11/2000 |
| WO | WO 00/71511 | 11/2000 |
| WO | WO 00/71535 | 11/2000 |
| WO | WO 01/14375 | 3/2001 |
| WO | WO 01/27089 | 4/2001 |
| WO | WO 01/34605 | 5/2001 |
| WO | WO 01/70695 | 9/2001 |
| WO | WO 01/87875 | 11/2001 |
| WO | WO 02/16359 | 2/2002 |
| WO | WO 02/40486 | 5/2002 |
| WO | WO 03/032970 | 4/2003 |
| WO | WO 03/032971 | 4/2003 |
| WO | WO 03/032972 | 4/2003 |
| WO | WO 03/032980 | 4/2003 |
| WO | WO 03/033298 | 4/2003 |
| WO | WO 03/033457 | 4/2003 |
| WO | WO 03/033482 | 4/2003 |
| WO | WO 03/033483 | 4/2003 |
| WO | WO 03/068747 | 8/2003 |
| WO | WO 03/093248 | 11/2003 |
| WO | WO 04/010995 | 2/2004 |
| WO | WO 04/089874 | 10/2004 |
| WO | WO 04/089875 | 10/2004 |
| WO | WO 04/089876 | 10/2004 |
| WO | WO 05/014550 | 2/2005 |
| WO | WO 05/073189 | 8/2005 |
| WO | WO 05/073217 | 8/2005 |
| WO | WO 05/073219 | 8/2005 |
| WO | WO 05/073232 | 8/2005 |

OTHER PUBLICATIONS

Ceccarelli et al., *European Journal of Medicinal Chemistry*, vol. 33 (12) pp. 943-955 (1998).
Gabriele et al., *European Journal of Organic Chemistry*, vol. 2001 (24) pp. 4607-4613 (2001).
Han et al., *Biohemica et Biophysica Acta—Molecular Cell Research*, vol. 1265 (2-3) pp. 224-227 (1995.
Hanson, *Expert Opinion on Therapeutic Patents*, vol. 7(7) pp. 729-733 (1997).
Henry et al., *Drugs of the Future*, vol. 24 (12) pp. 1345-1354 (1999).
Jiang et al, *Journal of Biological Chemistry*, vol. 271 (30) pp. 17920-17926 (1996).
Li et al., *Biochemical and Biophysical Research Communications*, vol. 228 (2) pp. 334-340 (1996).
Liebeskind et al., *Organic Letters*, vol. 4 (6) pp. 979-981 (2002).
Moreland et al., *Annals of Internal Medicine*, vol. 130 (6) pp. 478-486 (1999).
Murali Dhar et al., *Bioorganic and Medicinal Chemistry Letters*, vol. 12 (21) pp. 3125-3128 (2002).
Rankin et al., *British Journal of Rheumatology*, vol. 34, pp. 334-342 (1995).
Salituro et al., *Current Medicinal Chemistry*, vol. 6, pp. 807-823 (1999).
Wang et al., *Journal of Biological Chemistry*, vol. 272 (38) pp. 23668-23674 (1997).
Courtney, S. et al., *Bioorganic Medicinal Chemistry Letters*, vol. 14 pp. 3269-3273 (2004).
Foster, et al., *Drug News Perspect.*, vol. 13(8) pp. 488-497 (2000).
Marin, et al., *Blood*, vol. 98(3) pp. 667-673 (2001).
U.S. Appl. No. 10/513,095, filed Aug. 26, 2005, Angell et al.
U.S. Appl. No. 10/492,714, filed Apr. 15, 2004, Angell et al.
U.S. Appl. No. 10/568,121, filed Feb. 9, 2006, Walker, A.

U.S. Appl. No. 10/522,955, filed Nov. 11, 2005, Angell et al.
U.S. Appl. No. 10/551,503, filed Sep. 30, 2005, Aston, N.
U.S. Appl. No. 10/551,501, filed Sep. 30, 2005, Aston, N.
U.S. Appl. No. 10/551,502, filed Sep. 30, 2005, Aston et al.
Bochm, et al., Expert Opinion on Therapeutic Patents, vol. 10(1), pp. 25-37 (2000).
Hanson, G., Expert Opinion on Therapeutic Patents, vol. 7(7) pp. 729-733 (1997).
Henry, et al., Bioorganic & Medicinal Chemistry Letters, vol. 8 pp. 3335-3340 (1998).
Herlaar, et al., Molecular Medicine Today=, vol. 5 pp. 439-447 (1999).
Underwood, et al., Journal of Pharmacology and Experimental Therapeutics, vol. 293 (1) pp. 281-088 (2000).
Wadsworth, et al., Journal of Pharmacology and Experimental Therapeutics, vol. 291 (2) pp. 680-687 (1999).

2'-METHYL-5'-(1,3,4-OXADIAZOL-2-YL)-1,1'-BIPHENYL-4-CARBOXAMIDE DERIVATIVES AND THEIR USE AS P38 KINASE INHIBITORS

This application is filed Dursuant to 35 U.S.C. § 371 as a United States National Phase Application of International Application No. PCT/EP02/11575 filed Oct. 16, 2002, which claims Drioritv from GB 0124938.2 filed Oct. 17, 2001.

This invention relates to novel compounds and their use as pharmaceuticals, particularly as p38 kinase inhibitors, for the treatment of certain diseases and conditions.

We have now found a group of novel compounds that are inhibitors of p38 kinase.

According to the invention there is provided a compound of formula (I):

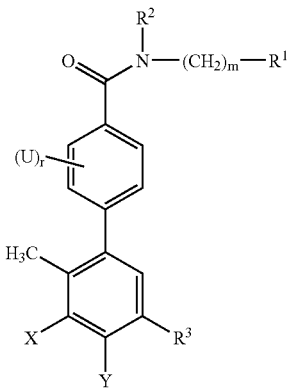

(I)

wherein
when m is 0 to 4 $R^1$ is selected from $C_{1-6}$alkyl, $C_{3-7}$cycloalkyl, $C_{2-6}$alkenyl, —$SO_2NR^4R^5$, —$CONR^4R^5$ and —$COOR^4$;
and when m is 2 to 4 $R^1$ is additionally selected from $C_{1-6}$alkoxy, hydroxy, $NR^4R^5$, —$NR^4SO_2R^5$, —$NR^4SOR^5$, —$NR^4COR^5$, and —$NR^4CONR^4R^5$;

$R^2$ is selected from hydrogen, $C_{1-6}$alkyl and —$(CH_2)_n$—$C_{3-7}$cycloalkyl;

$R^3$ is the group

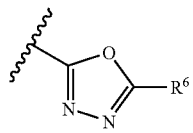

$R^4$ and $R^5$ are independently selected from hydrogen, $C_{1-6}$alkyl, heterocyclyl optionally substituted by $C_{1-4}$alkyl; and phenyl wherein the phenyl is optionally substituted by up to two groups independently selected from $C_{1-6}$alkoxy, $C_{1-6}$alkyl and halogen; or $R^4$ and $R^5$, together with the nitrogen atom to which they are bound, form a five- to six-membered heterocyclic or heteroaryl ring optionally containing one additional heteroatom selected from oxygen, sulfur and nitrogen, wherein the ring may be substituted by up to two $C_{1-6}$alkyl groups;

$R^6$ is selected from hydrogen and $C_{1-4}$alkyl;
U is selected from methyl and halogen;
X and Y are each selected independently from hydrogen, methyl and halogen;
m is selected from 0, 1, 2, 3 and 4 wherein each carbon atom of the resulting carbon chain may be optionally substituted with one or two groups selected independently from $C_{1-6}$alkyl;
n is selected from 0, 1, 2 and 3;
r is selected from 0, 1 and 2;
or a pharmaceutically acceptable salt or solvate thereof.

According to a further embodiment of the invention there is provided a compound of formula (IA):

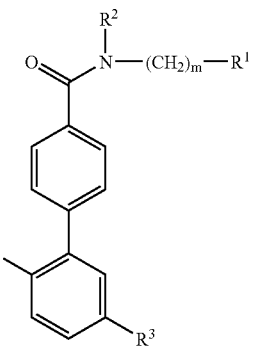

(IA)

wherein $R^1$, $R^2$, $R^3$ and m are as defined above, or a pharmaceutically acceptable salt or solvate thereof.

In a preferred embodiment, the molecular weight of a compound of formula (I) does not exceed 1000, more preferably 800, even more preferably 600.

In a preferred embodiment, $R^1$ is selected from $C_{1-4}$alkyl, in particular, methyl, or iso-propyl, $C_{3-6}$cycloalkyl, in particular cyclopropyl, cyclobutyl, cyclopentyl or cyclohexyl, —$CONHCH_3$, —$SO_2NH_2$, —$SO_2N(CH_3)_2$, methoxy, —$NHSO_2CH_3$ and —$NHCOCH_3$. In a further preferred embodiment, $R^1$ is selected from $C_{1-6}$alkyl, in particular 1,2-dimethylpropyl, isobutyl, 1-methylbutyl, 2-methylbutyl, 1,3-dimethylbutyl, 3,3-dimethylbutyl and n-pentyl; $C_{3-7}$cycloalkyl, in particular cyclopropyl, cyclobutyl or cyclohexyl; $C_{2-6}$alkenyl, in particular 2-methylallyl; —$CONR^4R^5$, in particular —$CONHCH_3$ or where $R^4$ and $R^5$ are independently selected from hydrogen, $C_{1-6}$alkyl and phenyl optionally substituted by up to two groups independently selected from $C_{1-6}$alkoxy; hydroxy; and $NR^4R^5$, in particular where $R^4$ and $R^5$ are independently selected from hydrogen and $C_{1-6}$alkyl.

In a preferred embodiment, $R^2$ is selected from hydrogen, $C_{1-4}$alkyl and —$CH_2$-cyclopropyl, more preferably hydrogen.

In a preferred embodiment, $R^4$ and $R^5$ are independently selected from hydrogen, $C_{1-4}$alkyl and phenyl. Particularly preferred are hydrogen and methyl. Further particularly preferred groups are hydrogen, ethyl and phenyl optionally substituted by up to two groups independently selected from $C_{1-6}$alkoxy.

In a preferred embodiment, $R^6$ is selected from $C_{1-4}$alkyl, more preferably methyl.

In a preferred embodiment, X and Y are each selected independently from hydrogen, chlorine and fluorine. In a further preferred embodiment, X is fluorine.

In a preferred embodiment, m is selected from 0, 1 and 2, and when the carbon chain of m is substituted, these substituents are preferably one or two methyls. A further preferred substituent for m is t-butyl.

In a preferred embodiment, r is selected from 0 and 1. In particular, r is 0.

It is to be understood that the present invention covers all combinations of particular and preferred groups described hereinabove.

Particular compounds according to the invention include those mentioned in the examples and their pharmaceutically acceptable salts and solvates. Specific examples which may be mentioned include:

N-(Cyclopropylmethyl)-2'-methyl-5'-(5-methyl-1,3,4-oxadiazol-2-yl)-1,1'-biphenyl-4-carboxamide;

N-(3,3-Dimethylbutyl)-2'-methyl-5'-(5-methyl-1,3,4-oxadiazol-2-yl)-1,1'-biphenyl-4-carboxamide; and N-(2,3-Dimethylcyclohexyl)-2'-methyl-5'-(5-methyl-1,3,4-oxadiazol-2-yl)-1,1'-biphenyl-4-carboxamide.

As used herein, the term "alkyl" refers to straight or branched hydrocarbon chains containing the specified number of carbon atoms. For example, $C_{1-6}$alkyl means a straight or branched alkyl containing at least 1, and at most 6, carbon atoms. Examples of "alkyl" as used herein include, but are not limited to, methyl, ethyl, n-propyl, n-butyl, n-pentyl, isobutyl, isopropyl and t-butyl. A $C_{1-4}$alkyl group is preferred, for example methyl, ethyl, isopropyl or t-butyl. The said alkyl groups may be optionally substituted with one or more fluorine atoms, for example, trifluoromethyl.

As used herein, the term "alkoxy" refers to a straight or branched chain alkoxy group, for example, methoxy, ethoxy, propoxy, prop-2-oxy, butoxy, but-2-oxy, 2-methylprop-1-oxy, 2-methyl prop-2-oxy, pentoxy, or hexyloxy. A $C_{1-4}$alkoxy group is preferred, for example methoxy or ethoxy.

As used herein, the term "cycloalkyl" refers to a non-aromatic hydrocarbon ring containing the specified number of carbon atoms which may optionally contain up to one double bond. For example, $C_{3-7}$cycloalkyl means a non-aromatic ring containing at least three, and at most seven, ring carbon atoms. Examples of "cycloalkyl" as used herein include, but are not limited to, cyclopropyl, cyclobutyl, cyclopentyl, cyclohexyl and cycloheptyl. A $C_{3-6}$ cycloalkyl group is preferred, for example, cyclopropyl, cyclopentyl or cyclohexyl. When $R^1$ is a $C_{3-7}$cycloalkyl group, the cycloalkyl group may be optionally substituted by one or more groups selected from $C_{1-6}$alkyl and phenyl.

As used herein, the term "alkenyl" refers to straight or branched hydrocarbon chains containing the specified number of carbon atoms and containing at least one double bond. For example, $C_{2-6}$alkenyl means a straight or branched alkenyl containing at least 2, and at most 6, carbon atoms and containing at least one double bond. Examples of "alkenyl" as used herein include, but are not limited to ethenyl and propenyl.

As used herein, the terms "heteroaryl ring" and "heteroaryl" refer to a monocyclic five- to seven-membered unsaturated ring containing at least one heteroatom selected from oxygen, nitrogen and sulfur. Preferably, the heteroaryl ring has five or six ring atoms. Examples of heteroaryl rings include, but are not limited to, furyl, thienyl, pyrrolyl, oxazolyl, thiazolyl, isoxazolyl, isothiazolyl, imidazolyl, pyrazolyl, oxadiazolyl, triazolyl, tetrazolyl, thiadiazolyl, pyridyl, pyridazinyl, pyrimidinyl, pyrazinyl and triazinyl. The said ring may be optionally substituted by one or more substituents independently selected from $C_{1-6}$alkyl and oxy.

As used herein, the term "heterocyclic ring" and "heterocyclyl" refer to a monocyclic three- to seven-membered saturated or non-aromatic, unsaturated hydrocarbon ring containing at least one heteroatom independently selected from oxygen, nitrogen and sulfur. Preferably, the heterocyclyl ring has five or six ring atoms. Examples of heterocyclyl groups include, but are not limited to, aziridinyl, pyrrolinyl, pyrrolidinyl, imidazolinyl, imidazolidinyl, pyrazolinyl, pyrazolidinyl, piperidyl, piperazinyl, morpholino, and thiomorpholino. The said ring may be optionally substituted by one or more substituents independently selected from $C_{1-6}$alkyl and oxy.

As used herein, the term "fused bicyclic ring" refers to a ring system comprising two five- to seven-membered saturated or unsaturated hydrocarbon rings, the ring system containing at least one heteroatom independently selected from oxygen, nitrogen and sulfur. Examples of suitable fused bicyclic rings include, but are not limited to, naphthyl, indolyl, indolinyl, benzothienyl, quinolyl, isoquinolyl, tetrahydroquinolyl, benzodioxanyl, indanyl and tetrahydronaphthyl. Each ring may be optionally substituted with one or more substituents selected from halogen, $C_{1-6}$alkyl, oxy, $-(CH_2)_p NR^{10}R^{11}$, $-CO(CH_2)_p NR^{10}R^{11}$, and imidazolyl; and p is selected from 0 and 1. Particularly preferred substituents are chlorine, imidazolyl and $-CH_2-N(CH_3)_2$.

As used herein, the terms "halogen" or "halo" refer to the elements fluorine, chlorine, bromine and iodine. Preferred halogens are fluorine, chlorine and bromine. A particularly preferred halogen is fluorine.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "solvate" refers to a complex of variable stoichiometry formed by a solute (in this invention, a compound of formula (I) or a salt thereof) and a solvent. Such solvents for the purpose of the invention may not interfere with the biological activity of the solute. Examples of suitable solvents include water, methanol, ethanol and acetic acid. Preferably the solvent used is a pharmaceutically acceptable solvent. Examples of suitable pharmaceutically acceptable solvents include water, ethanol and acetic acid. Most preferably the solvent used is water.

Certain compounds of formula (I) may exist in stereoisomeric forms (e.g. they may contain one or more asymmetric carbon atoms or may exhibit cis-trans isomerism). The individual stereoisomers (enantiomers and diastereomers) and mixtures of these are included within the scope of the present invention. The present invention also covers the individual isomers of the compounds represented by formula (I) as mixtures with isomers thereof in which one or more chiral centres are inverted. Likewise, it is understood that compounds of formula (I) may exist in tautomeric forms other than that shown in the formula and these are also included within the scope of the present invention.

Salts of the compounds of the present invention are also encompassed within the scope of the invention and may, for example, comprise acid addition salts resulting from reaction of an acid with a nitrogen atom present in a compound of formula (I).

Salts encompassed within the term "pharmaceutically acceptable salts" refer to non-toxic salts of the compounds of this invention. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isethionate, Lactate, Lactobionate, Laurate, Malate, Maleate, Mandelate, Mesylate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. Other salts which are not pharmaceutically acceptable may be useful in the preparation of compounds of this invention and these form a further aspect of the invention.

The compounds of this invention may be made by a variety of methods, including standard chemistry. Any previously defined variable will continue to have the previously defined meaning unless otherwise indicated. Illustrative general synthetic methods are set out below and then specific compounds of the invention are prepared in the working Examples.

For example, a general method (A) for preparing the compounds of Formula (I) comprises the reactions set out in Scheme 1 below.

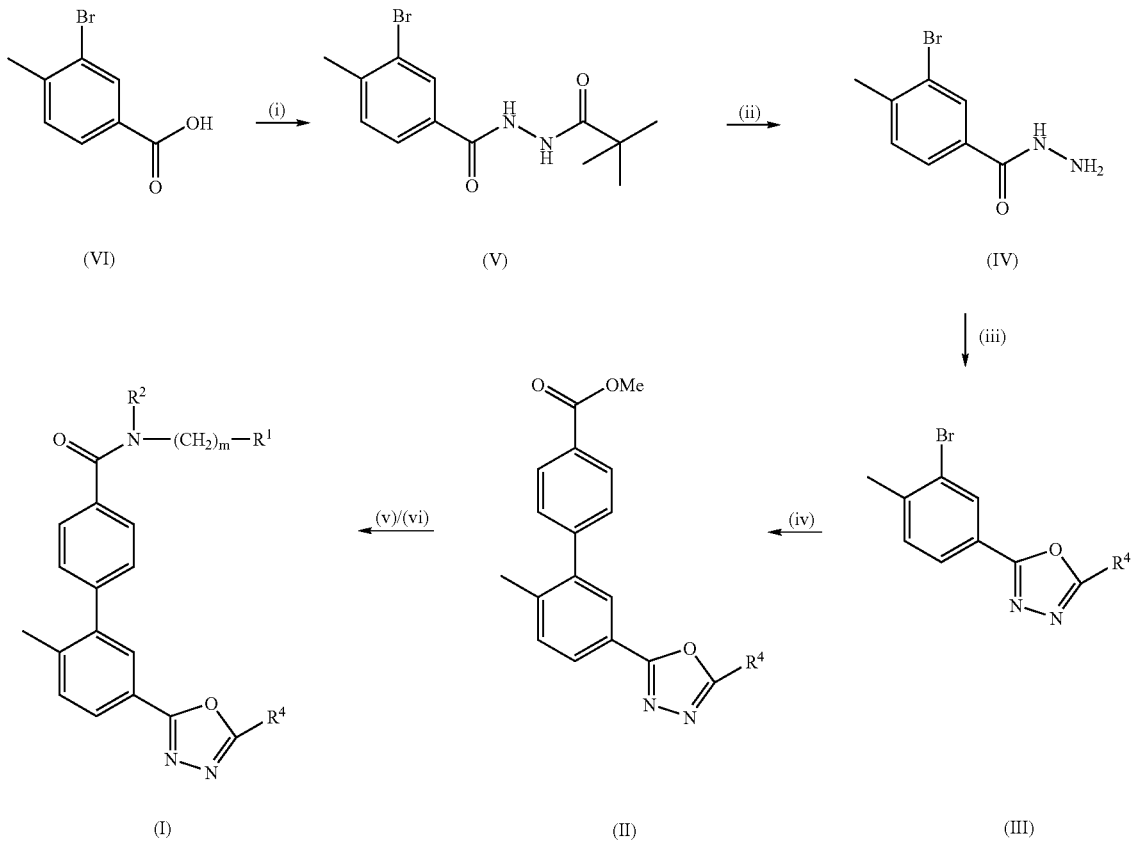

(i) t-butyl carbazate, HOBT, HBTU, DIPEA, DMF
(ii) TFA
(iii) $R^4C(OEt)_3$
(iv) (4-Methoxycarbonylphenyl)boronic acid, $(Ph_3P)_4Pd$, $CsCO_3$, DME
(v) LiOH, THF, $H_2O$
(vi) $R^1(CH_2)_mN$ $R^2H$, HOBT, HBTU, DIPEA, DMF For example, a general method (B) for preparing the compounds of Formula (I) comprises the reactions set out in Scheme 2 below.

Scheme 2
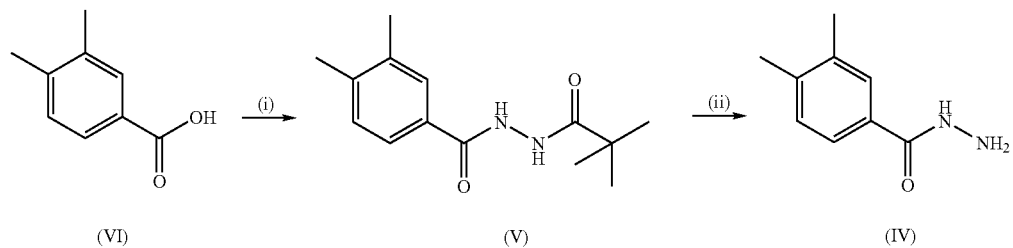
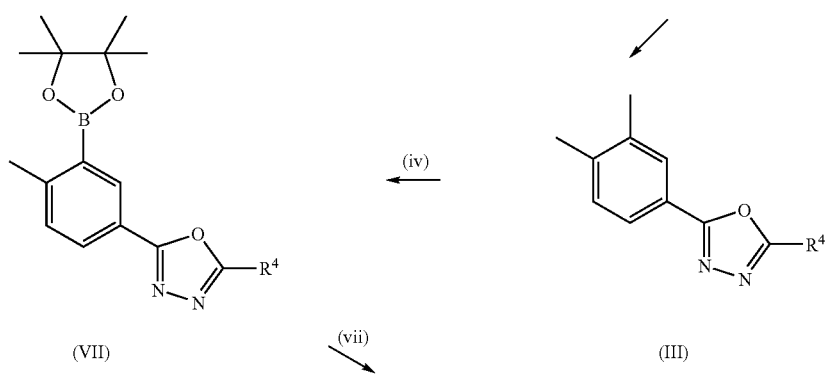
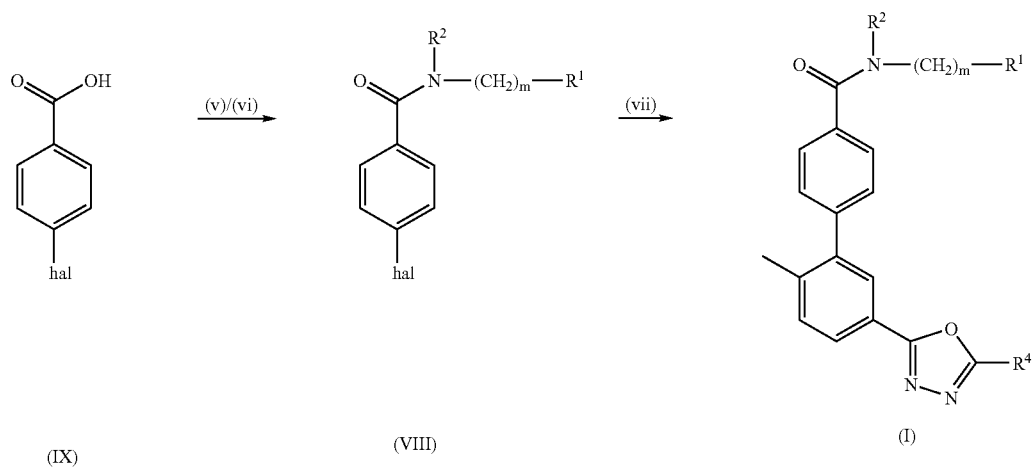
(i) t-butyl carbazate, HOBT, HBTU, DIPEA, DMF
(ii) TFA
(iii) R$^4$C(OEt)$_3$
(iv) Bis(pinacolato)diboron, KOAc, PdCl$_2$dppf, DMF
(v) SOCl$_2$
(vi) R$^1$(CH$_2$)$_m$X(CH$_2$)$_n$N R$^2$H, Na$_2$CO$_3$, acetone
(vii) (Ph$_3$P)$_4$Pd, Na$_2$CO$_3$, DMF
For example, a general method (C) for preparing the compounds of Formula (I) comprises the reactions set out in Scheme 3 below.

Scheme 3

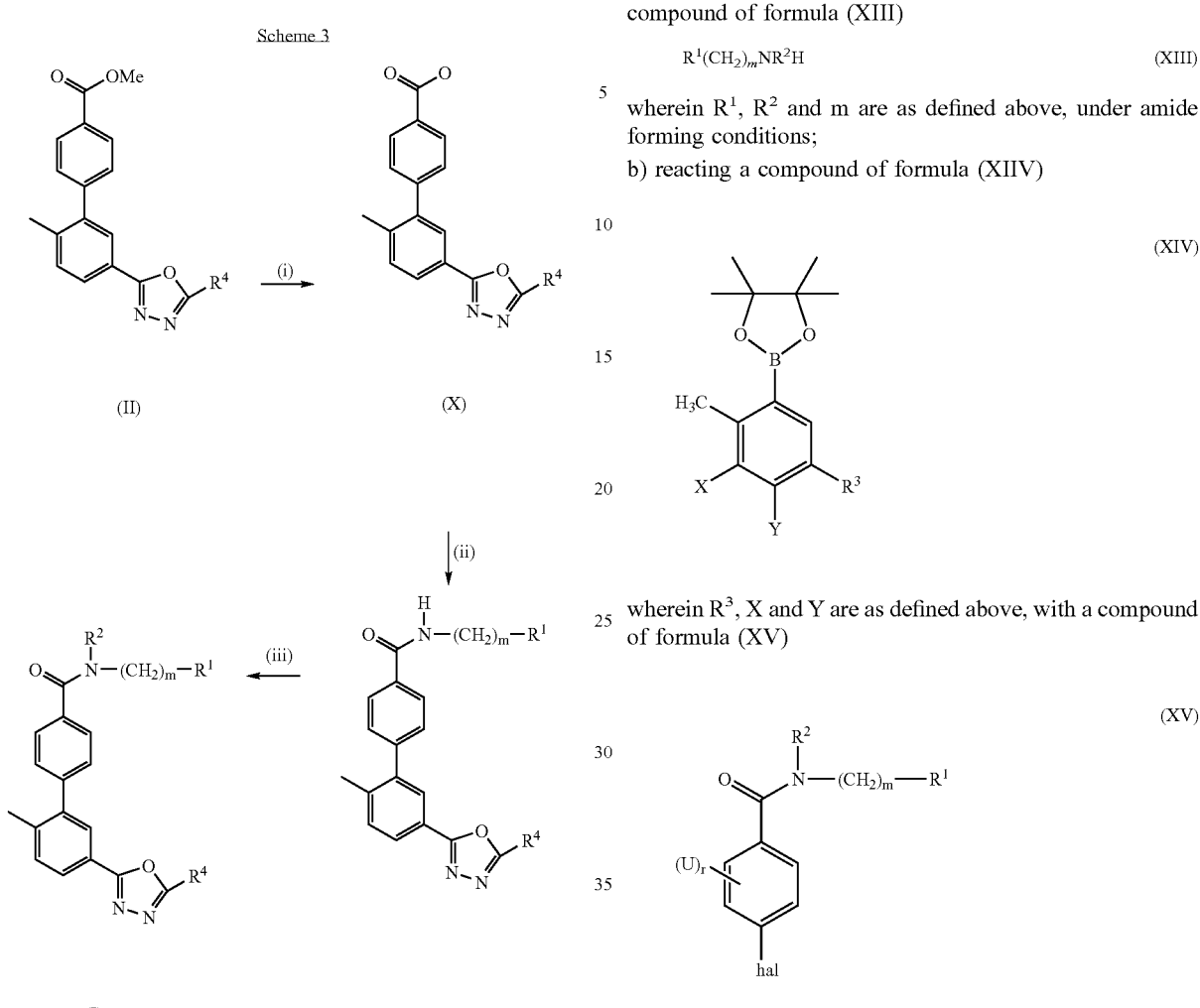

(i) LiOH, THF, H₂O
(ii) R¹(CH₂)$_m$NH₂, HOBT, HBTU, DIPEA, DMF
(iii) R²-hal, NaH, DMF Thus, according to the invention there is provided a process for preparing a compound of formula (I) which comprises:

(a) reacting a compound of formula (XII)

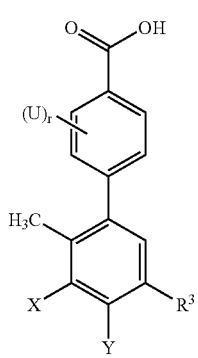

(XII)

wherein R³, U, X, Y and r are as defined above, with a compound of formula (XIII)

$$R^1(CH_2)_mNR^2H \qquad (XIII)$$

wherein R¹, R² and m are as defined above, under amide forming conditions;

b) reacting a compound of formula (XIIV)

(XIV)

wherein R³, X and Y are as defined above, with a compound of formula (XV)

(XV)

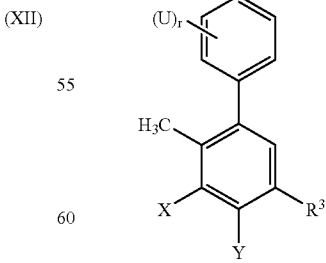

wherein R¹, R², U, m and r are as defined above and hal is halogen, in particular bromine or iodine, in the presence of a catalyst, for example tetrakis(triphenylphosphine)palladium; or c) reacting a compound of formula (XVI)

(XVI)

wherein R³, U, X, Y and r are as defined above, with a compound of formula (XVII)

$$R^1(CH_2)_mNH_2 \qquad (XVII)$$

wherein R¹ and m are as defined above, under amide forming conditions, followed by reaction with a compound of formula (XVIII)

$$R^2\text{-hal} \qquad\qquad\qquad (XIII)$$

in which $R^2$ and hal are as defined above, in the presence of a base such as sodium hydride.

Suitable amide forming conditions are well known in the art and include treating a solution of the acid, in for example DMF, with an amine in the presence of, for example, HOBT, HBTU and DIPEA.

Whilst it is possible for the compounds, salts or solvates of the present invention to be administered as the new chemical, the compounds of formula (I) and their pharmaceutically acceptable salts and solvates are conveniently administered in the form of pharmaceutical compositions. Thus, in another aspect of the invention, we provide a pharmaceutical composition comprising a compound of formula (I) or a pharmaceutically acceptable salt or solvate thereof, in admixture with one or more pharmaceutically acceptable carriers, diluents or excipients.

The compounds of formula (I) and their pharmaceutically acceptable salts and solvates may be formulated for administration in any suitable manner. They may, for example, be formulated for topical administration or administration by inhalation or, more preferably, for oral, transdermal or parenteral administration. The pharmaceutical composition may be in a form such that it can effect controlled release of the compounds of formula (I) and their pharmaceutically acceptable salts and solvates. A particularly preferred method of administration, and corresponding formulation, is oral administration.

For oral administration, the pharmaceutical composition may take the form of, and be administered as, for example, tablets (including sub-lingual tablets) and capsules (each including timed release and sustained release formulations), pills, powders, granules, elixirs, tinctures, emulsions, solutions, syrups or suspensions prepared by conventional means with acceptable excipients.

For instance, for oral administration in the form of a tablet or capsule, the active drug component can be combined with an oral, non-toxic pharmaceutically acceptable inert carrier such as ethanol, glycerol, water and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules can be made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additives such as peppermint oil or saccharin, and the like can also be added.

Where appropriate, dosage unit formulations for oral administration can be microencapsulated. The formulation can also be prepared to prolong or sustain the release as for example by coating or embedding particulate material in polymers, wax or the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be administered in the form of liposome emulsion delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolyllysine substituted with palmitoyl residues. Furthermore, the compounds of the present invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

The present invention includes pharmaceutical compositions containing 0.1 to 99.5%, more particularly, 0.5 to 90% of a compound of the formula (I) in combination with a pharmaceutically acceptable carrier.

Likewise, the composition may also be administered in nasal, ophthalmic, otic, rectal, topical, intravenous (both bolus and infusion), intraperitoneal, intraarticular, subcutaneous or intramuscular, inhalation or insufflation form, all using forms well known to those of ordinary skill in the pharmaceutical arts.

For transdermal administration, the pharmaceutical composition may be given in the form of a transdermal patch, such as a transdermal iontophoretic patch.

For parenteral administration, the pharmaceutical composition may be given as an injection or a continuous infusion (e.g. intravenously, intravascularly or subcutaneously). The compositions may take such forms as suspensions, solutions or emulsions in oily or aqueous vehicles and may contain formulatory agents such as suspending, stabilizing and/or dispersing agents. For administration by injection these may take the form of a unit dose presentation or as a multidose presentation preferably with an added preservative. Alternatively for parenteral administration the active ingredient may be in powder form for reconstitution with a suitable vehicle.

The compounds of the invention may also be formulated as a depot preparation. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

Alternatively the composition may be formulated for topical application, for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

The pharmaceutical compositions generally are administered in an amount effective for treatment or prophylaxis of a specific condition or conditions. Initial dosing in human is accompanied by clinical monitoring of symptoms, such symptoms for the selected condition. In general, the compositions are administered in an amount of active agent of at least about 100 µg/kg body weight In most cases they will be administered in one or more doses in an amount not in excess of about 20 mg/kg body weight per day. Preferably, in most cases, dose is from about 100 µg/kg to about 5 mg/kg body weight, daily. For administration particularly to mammals, and particularly humans, it is expected that the daily dosage level of the active agent will be from 0.1 mg/kg to 10 mg/kg and typically around 1 mg/kg. It will be appreciated that optimum dosage will be determined by standard methods for each treatment modality and indication, taking into account the indication, its severity, route of administration, complicating conditions and the like. The physician in any event will determine the actual dosage which will be most suitable for an individual and will vary with the age, weight and response of the particular individual. The effectiveness of a selected actual dose can readily be determined, for example, by measuring clinical symptoms or standard ant-inflammatory indicia after administration of the selected dose. The above dosages are exemplary of the average case. There can, of course, be individual instances where higher or lower dosage ranges are merited, and such are within the scope of this invention. For conditions or disease states as are treated by the present invention, maintaining consistent daily levels in a subject over an extended period of time, e.g., in a maintenance regime, can be particularly beneficial.

In another aspect, the present invention provides a compound of formula (I) or a salt or solvate thereof, for use in therapy.

The compounds of the present invention are generally inhibitors of the serine/threonine kinase p38 and are therefore also inhibitors of cytokine production which is mediated by p38 kinase. Within the meaning of the term "inhibitors of the serine/threonine kinase p38" are included those compounds that interfere with the ability of p38 to transfer a phosphate group from ATP to a protein substrate according to the assay described below.

It will be appreciated that the compounds of the invention may be selective for one or more of the isoforms of p38, for example p38α, p38β, p38γ and/or p38δ. In one embodiment, the compounds of the invention selectively inhibit the p38α isoform. In another embodiment, the compounds of the invention selectively inhibit the p38β isoform. In a further embodiment, the compounds of the invention selectively inhibit the p38α and p38β isoforms. Assays for determining the selectivity of compounds for the p38 isoforms are described in, for example, WO 99/61426, WO 00/171535 and WO 02/46158.

It is known that p38 kinase activity can be elevated (locally or throughout the body), p38 kinase can be incorrectly temporally active or expressed, p38 kinase can be expressed or active in an inappropriate location, p38 kinase can be constitutively expressed, or p38 kinase expression can be erratic; similarly, cytokine production mediated by p38 kinase activity can be occurring at inappropriate times, inappropriate locations, or it can occur at detrimentally high levels.

Accordingly, the present invention provides a method for the treatment of a condition or disease state mediated by p38 kinase activity, or mediated by cytokines produced by the activity of p38 kinase, in a subject which comprises administering to said subject a therapeutically effective amount of a compound of formula (I) or a pharmaceutically acceptable salt or solvate thereof. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention also provides a method of inhibiting cytokine production which is mediated by p38 kinase activity in a subject, e.g. a human, which comprises administering to said subject in need of cytokine production inhibition a therapeutic, or cytokine-inhibiting, amount of a compound of the present invention. The compound may be administered as a single or polymorphic crystalline form or forms, an amorphous form, a single enantiomer, a racemic mixture, a single stereoisomer, a mixture of stereoisomers, a single diastereoisomer or a mixture of diastereoisomers.

The present invention treats these conditions by providing a therapeutically effective amount of a compound of this invention. By "therapeutically effective amount" is meant a symptom-alleviating or symptom-reducing amount, a cytokine-reducing amount, a cytokine-inhibiting amount, a kinase-regulating amount and/or a kinase-inhibiting amount of a compound. Such amounts can be readily determined by standard methods, such as by measuring cytokine levels or observing alleviation of clinical symptoms. For example, the clinician can monitor accepted measurement scores for anti-inflammatory treatments.

The compounds of the present invention can be administered to any subject in need of inhibition or regulation of p38 kinase or in need of inhibition or regulation of p38 mediated cytokine production. In particular, the compounds may be administered to mammals. Such mammals can include, for example, horses, cows, sheep, pigs, mice, dogs, cats, primates such as chimpanzees, gorillas, rhesus monkeys, and, most preferably, humans.

Thus, the present invention provides methods of treating or reducing symptoms in a human or animal subject suffering from, for example, rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, cancer including breast cancer, colon cancer, lung cancer or prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer, which comprises administering to said subject a therapeutically effective amount of a compound of formula (I) or a pharmaceutically acceptable salt or solvate thereof.

A further aspect of the invention provides a method of treatment of a human or animal subject suffering from rheumatoid arthritis, neurodegenerative disease, Alzheimer's disease, Parkinson's disease and epilepsy which comprises administering to said subject a therapeutically effective amount of a compound of formula (I) or a pharmaceutically acceptable salt or solvate thereof.

A further aspect of the invention provides a method of treatment of a human or animal subject suffering from any type of pain including chronic pain, rapid onset of analgesis, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain which comprises administering to said subject a therapeutically effective amount of a compound of formula (I) or a pharmaceutically acceptable salt or solvate thereof.

A further aspect of the invention provides the use of a compound of formula (I), or a pharmaceutically acceptable salt or solvate thereof, for the preparation of a medicament for the treatment of a condition or disease state mediated by p38 kinase activity or mediated by cytokines produced by p38 kinase activity.

A further aspect of the invention provides the use of a compound of formula (I), or a pharmaceutically acceptable salt or solvate thereof, for the preparation of a medicament for the treatment of a condition or disease state selected from rheumatoid arthritis, osteoarthritis, asthma, psoriasis, eczema, allergic rhinitis, allergic conjunctivitis, adult respiratory distress syndrome, chronic pulmonary inflammation, chronic obstructive pulmonary disease, chronic heart failure, silicosis, endotoxemia, toxic shock syndrome, inflammatory bowel disease, tuberculosis, atherosclerosis, neurodegenerative disease, Alzheimer's disease, Parkinson's disease, Huntington's disease, amyotrophic lateral sclerosis, epilepsy, multiple sclerosis, aneurism, stroke, irritable bowel syndrome, muscle degeneration, bone resorption diseases, osteoporosis, diabetes, reperfusion injury, graft vs. host reaction, allograft rejections, sepsis, systemic cachexia, cachexia secondary to infection or malignancy, cachexia secondary to aquired immune deficiency syndrome (AIDS), malaria, leprosy, infectious arthritis, leishmaniasis, Lyme disease, glomerulonephritis, gout, psoriatic arthritis, Reiter's syndrome, traumatic arthritis, rubella arthritis, Crohn's disease, ulcerative colitis, acute synovitis, gouty arthritis, spondylitis, and non articular inflammatory conditions, for example, herniated/ruptured/prolapsed intervertebral disk syndrome, bursitis, tendonitis, tenosynovitis, fibromyalgic syndrome and other inflammatory conditions associated with ligamentous sprain and regional musculoskeletal strain, pain, for example that associated with inflammation and/or trauma, osteopetrosis, restenosis, thrombosis, angiogenesis, and cancer including breast cancer, colon cancer, lung cancer or prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease, neurodegenerative disease, Alzheimer's disease, Parkinson's disease, epilepsy, and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, asthma, psoriasis, chronic pulmonary inflammation, chronic obstructive pulmonary disease, chronic heart failure, systemic cachexia, glomerulonephritis, Crohn's disease and cancer including breast cancer, colon cancer, lung cancer and prostatic cancer.

A further aspect of the invention provides the use of a compound of formula (I), or a pharmaceutically acceptable salt or solvate thereof, for the preparation of a medicament for the treatment of a condition or disease state selected from rheumatoid arthritis, neurodegenerative disease, Alzheimer's disease, Parkinson's disease and epilepsy.

A further aspect of the invention provides the use of a compound of formula (I), or a pharmaceutically acceptable salt or solvate thereof, for the preparation of a medicament for the treatment of any type of pain including chronic pain, rapid onset of analgesia, neuromuscular pain, headache, cancer pain, acute and chronic inflammatory pain associated with osteoarthritis and rheumatoid arthritis, post operative inflammatory pain, neuropathic pain, diabetic neuropathy, trigeminal neuralgia, post-hepatic neuralgia, inflammatory neuropathies and migraine pain.

The compounds of formula (I) and their salts, solvates and physiologically functional salts and solvates may be employed alone or in combination with other therapeutic agents for the treatment of the above-mentioned conditions. In particular, in rheumatoid arthritis therapy, combination with other chemotherapeutic or antibody agents is envisaged. Combination therapies according to the present invention thus comprise the administration of at least one compound of formula (I) or a pharmaceutically acceptable salt or solvate thereof and at least one other pharmaceutically active agent The compound(s) of formula (I) or pharmaceutically acceptable salt(s) or solvate(s) thereof and the other pharmaceutically active agent(s) may be administered together or separately and, when administered separately, this may occur separately or sequentially in any order. The amounts of the compound(s) of formula (I) or pharmaceutically acceptable salt(s) or solvate(s) thereof and the other pharmaceutically active agent(s) and the relative timings of administration will be selected in order to achieve the desired combined therapeutic effect. Examples of other pharmaceutically active agents which may be employed in combination with compounds of formula (I) and their salts and solvates for rheumatoid arthritis therapy include: immunosuppresants such as amtolmetin guacil, nizoribine and rimexolone; anti-TNFα agents such as etanercept, infliximab, diacerein; tyrosine kinase inhibitors such as leflunomide; kallikrein antagonists such as subreum; interleukin 11 agonists such as oprelvekin; interferon beta 1 agonists; hyaluronic acid agonists such as NRD-101 (Aventis); interleukin 1 receptor antagonists such as anakinra; CD8 antagonists such as amiprilose hydrochloride; beta amyloid precursor protein antagonists such as reumacon; matrix metalloprotease inhibitors such as cipemastat and other disease modifying anti-rheumatic drugs (DMARDs) such as methotrexate, sulphasalazine, cyclosporin A, hydroxychoroquine, auranofin, aurothioglucose, gold sodium thiomalate and penicillamine.

EXAMPLES

The following examples are illustrative embodiments of the invention, not limiting the scope of the invention in any way. Reagents are commercially available or are prepared according to procedures in the literature.

LCMS was conducted on a column (3.3 cm×4.6 mm ID, 3 um ABZ+PLUS), at a Flow Rate of 3 ml/min, Injection Volume of 5 μl, at room temperature and UV Detection Range at 215 to 330 nm.

General Method A:

A suspension of the hydrazide (4.36 mmol) in triethylorthoacetate (20 ml) was warmed at 100° C. for 2 h and then at 130° C. for 1.5 h. The excess triethylorthoacetate was removed under vacuum and the residue partitioned between ethyl acetate (50 ml) and water (50 ml). The organic material was washed with water (50 ml), brine (50 ml) and dried with magnesium sulphate. The solution was reduced to dryness under vacuum and the residue triturated with cyclohexane to give the oxadiazole.

General Method B:

The t-butoxycarbonylhydrazide (7.57 mmol) was added portionwise to a solution of trifluoroacetic acid at 0° C. Once addition was complete, the solution was stirred at 0° C. for 15 min and then at room temperature for 30 min. The solution was reduced to dryness under vacuum and the residue partitioned between ethyl acetate (100 ml) and sodium carbonate solution (2N, 100 ml). The aqueous fraction was extracted with ethyl acetate (2×75 ml). The combined organic fractions were washed with brine (100 ml), dried (magnesium sulphate) and evaporated to dryness under vacuum to give the hydrazide.

General Method C:

N,N-Disopropylethylamine (69.75 mmol) was added dropwise to a solution of benzoic acid (23.25 mmol), HOBT (23.25 mmol), t-butylcarbazate (23.25 mmol), HBTU (27.9 mmol) in DMF (15 ml) at 0° C. The reaction was stirred at 0° C. for 15 min and then at room temperature for 6 h. The DMF was evaporated under vacuum and the residue partitioned between DCM (150 ml) and water (150 ml). The aqueous fraction was extracted with DCM (2×100 ml). The combined organic fractions were washed with brine (100 ml), dried (magnesium sulphate) and evaporated to dryness under vacuum. The solid residue was washed with aqueous sodium carbonate (2N) and dried.

General Method D:

The aromatic bromide or iodide (4.0 mmol), phenylboronic acid (4.8 mmol), tetrakis(triphenylphosphine)palladium (100 mg) and caesium carbonate (2.4 g) in DME (30 ml) were heated at 90° C. under nitrogen for 20 h. The cooled reaction was preabsorbed onto silica and chromatographed on a silica SPE (10 g) eluting with an ethyl acetate/cyclohexane gradient (0–100% ethyl acetate). The combined product fractions were evaporated to dryness under vacuum.

General Method E:

The methyl benzoate (1.0 mmol) was dissolved in THF (10 ml) and a solution of lithium hydroxide monohydrate (2.1 mmol) in water (10 ml) added. The reaction mixture was heated at 75° C. for 4 h. The THF was evaporated under vacuum and the solution acidified with hydrochloric acid (2N). The precipitate formed was filtered off, washed with water and dried under vacuum.

General Method F:

Benzoic acid (0.1 mmol), HOBT (0.1 mmol), PyBOP (0.1 mmol) and amine (1.2 mmol) were mixed in 1.75 ml of DMF and DIPEA (52 µl) added, the reaction was stirred at room temperature for 72 h. The DMF was evaporated under vacuum and the residue partitioned between DCM and aqueous sodium hydrogen carbonate solution. The organic fraction was separated and the solution evaporated to dryness under vacuum. The residue was chromatographed on a silica SPE eluting with a DCM/ethanol/ammonia gradient (500:8:1 to 40:8:1). The product fractions were combined and evaporated to dryness. The residue was rechromatographed on silica SPE eluting with an ethyl acetate/cyclohexane gradient (1:8 to 1:1). Product fractions evaporated to dryness under vacuum.

General Method G:

Benzoic acid (3.1 mmol), HATU (3.7 mmol), DIPEA (6.8 mmol), and amine (3.1 mmol) were mixed in DMF (30 ml) and heated for 18 h at 80° C. The solvent was evaporated from the cooled reaction under vacuum and the residue dissolved in DCM. The DCM solution was washed with aqueous sodium hydroxide (2M), hydrochloric acid (2M) and brine. Dried with magnesium sulphate and the solvent evaporated under vacuum. The residue was chromatographed on silica eluting with DCM/ethanol/ammonia (500:8:1) and the solvent evaporated under vacuum from the product fractions.

General Method H:

Secondary amide (0.06 mmol), iodoalkane or bromoalkane (3 drops) and sodium hydride, (60% in mineral oil, 0.5 mmol) were stirred in DMF (5 ml) for 18 h. The reaction was acidified with hydrochloric acid (2N) and extracted with DCM (2×10 ml). The DCM was evaporated from the combined extracts under vacuum and the residue purified by SPE (silica, 1 g) eluting with ethylacetate. The ethyl acetate was evaporated under vacuum to give the tertiary amide.

General Method I:

Benzoic acid (0.1 mmol), HATU (0.1 mmol), DIPEA (0.3 mmol), and amine (0.12 mmol) were mixed in THF (5 ml) and heated for 16 h at room temperature. The solvent was evaporated under vacuum and the residue dissolved in DCM. The DCM solution was washed with aqueous sodium carbonate (2M), absorbed onto a silica SPE (5 g) and eluted with a DCM/ethanol,/ammonia gradient (500:8:1–15:8:1). The solvent was evaporated under vacuum from the product fractions to give the amide.

Example 1

N-(3-Hydroxypropyl)-2'-methyl-5'-(5-methyl-1,3,4-oxadiazol-2-yl)-1,1'-biphenyl-4-carboxamide a) 2'-Methyl-5'-(5-methyl-1,3,4-oxadiazol-2-yl)-1,1'-biphenyl-4-carboxylic acid (59 mg, 0.2 mmol), 3-amino-1-propanol (15 mg, 0.2 mmol) and 1-(3-dimethylaminopropyl)-3-ethyl carbodiimide hydrochloride (0.2 mmol) were suspended in dry DCM (7 ml) and stirred at room temperature under nitrogen for 20 h. 3-Amino-1-propanol (45 mg, 0.6 mmol) was added and the reaction stirred at room temperature for 21 h. 1-Hydroxybenzotriazole (27 mg, 0.2 mmol) was added and the reaction heated at 35° C. for 70 h. Water (10 ml) was added to the cooled reaction, and the organic fraction separated. The organic phase was absorbed onto a silica flash column and eluted with a DCM/ethanol/ammonia gradient (300:8:1 to 150:8:1). Solvent was evaporated from the product fractions under vacuum to give N-(3-hydroxypropyl)-2'-methyl-5'-(5-methyl-1,3,4-oxadiazol-2-yl)-1,1'-biphenyl-4-carboxamide (21 mg, 30%).

NMR; δH[$^2$H$_6$]-DMSO 8.52, (1H, t), 7.94–7.88, (3H, m), 7.75, (1H, m), 7.55 –7.49, (3H, m), 3.47, (2H, t), 3.33, (2H, m), 2.56, (3H, s), 2.30, (3H, s), 1.69, (2H, m). LCMS; retention time 2.68 min, MH$^+$ 352.

b) 2'-Methyl-5'-(5-methyl-1,3,4-oxadiazol-2-yl)-1,1'-biphenyl-4-carboxylic acid 2'-Methyl-5'-(5-methyl-1,3,4-oxadiazol-2-yl)-1,1'-biphenyl-4-carboxylic acid was prepared from methyl 2'-methyl-5'-(5-methyl-1,3,4-oxadiazol-2-yl)-1,1'-biphenyl-4-carboxylate using method E.

NMR; δH[$^2$H$_6$]-DMSO 8.03, (2H, d), 7.90, (1H, dd), 7.75, (1H, d), 7.57–7.52, (3H, m), 2.56, (3H, s), 2.30, (3H, s). LCMS; retention time 3.14 min, MH$^+$ 295.

c) Methyl 2'-methyl-5'-(5-methyl-1,3,4-oxadiazol-2-yl)-1,1'-biphenyl-4-carboxylate Methyl 2'-methyl-5'-(5-methyl-1,3,4-oxadiazol-2-yl)-1,1'-biphenyl-4-carboxylate was prepared from 2-(3-bromo-4-methylphenyl)-5-methyl-1,3,4-oxadiazole and (4-methoxycarbonylphenyl)boronic acid using method D.

NMR; δH CDCl$_3$ 8.12, (2H, d), 7.94, (1H, dd), 7.90, (1H, d), 7.43, (3H, m), 3.96, (3H, s), 2.61, (3H, s), 2.33, (3H, s). LCMS; retention time 3.37 min, MH$^+$ 309.

d) 2-(3-Bromo-4-methylphenyl)-5-methyl-1,3,4-oxadiazole 2-(3-Bromo-4-methylphenyl)-5-methyl-1,3,4-oxadiazole was prepared from (3-bromo-4-methylbenzoyl)hydrazine using method A.

NMR; δH[$^2$H$_6$]-DMSO 8.08, (1H, d), 7.86, (1H, dd), 7.56, (1H, d), 2.56, (3H, s), 2.41, (3H, s). LCMS; retention time 3.19 min, MH$^+$ 254.

e) (3-Bromo-4-methylbenzoyl)hydrazine (3-Bromo-4-methylbenzoyl)hydrazine was prepared from t-butyl 2-(3-bromo-4-methylbenzoyl)hydrazine-1-carboxylate using method B.

NMR; δH[$^2$H$_6$]-DMSO 9.82, (1H, b), 8.00, (1H, d), 7.73, (1H, dd), 7.42, (1H, d), 4.49, (2H, b), 2.36, (3H, s). LCMS; retention time 2.47 min.

f) t-Butyl 2-(3-bromo-4-methylbenzoyl)hydrazine-1-carboxylate t-Butyl 2-(3-bromo-4-methylbenzoyl)hydrazine-1-carboxylate was prepared from 3-bromo-4-methylbenzoic acid using method C.

NMR; δH[$^2$H$_6$]-DMSO 10.25, (1H, b), 8.94, (1H, b), 8.04, (1H, s), 7.76, (1H, d), 7.47, (1H, d), 2.39, (3H, s), 1.41, (9H,s). LCMS; retention time 3.24 min, MH$^+$ 330.

Example 2

N-(Cyclopropyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (59 mg, 0.2 mmol), cyclopropylamine (11 mg, 0.2 mmol) and 1-(3-dimethylaminopropyl)-3-ethyl carbodiimide hydrochloride (0.2 mmol) were suspended in dry DCM (7 ml) and stirred at room temperature under nitrogen for 20 h. Cyclopropylamine (33 mg, 0.6 mmol) was added and the reaction stirred at room temperature for 21 h. 1-Hydroxybenzotriazole (27 mg, 0.2 mmol) was added and the reaction heated at 35° C. for 70 h. Water (10 ml) was added to the cooled reaction, and the organic fraction separated. The organic phase was absorbed onto a silica flash column and eluted with DCl/ethanol/ammonia (300:8:1). Solvent was evaporated from the product fractions under vacuum to give N-(cyclopropyl)-2'-methyl-5'-(5-methyl-1,3,4-oxadiazol-2-yl)-1,1'-biphenyl-4-carboxamide (26 mg, 39%).

NMR; $\delta H[^2H_6]$-DMSO 8.51, (1H, d), 7.92–7.88, (3H, m), 7.75, (1H, d), 7.54, (1H, d), 7.48,(2H, d), 2.87, (1H, m), 2.56, (3H, s), 2.30, (3H, s), 0.71, (2H, m), 0.59, (2H, m). LCMS; retention time 2.89 min, MH$^+$ 334.

Example 3

N-[(Dimethylamino)propyl]-2'-methyl-5'-(5-methyl-1,3,4-oxadiazol-2-yl)-1,1'-biphenyl-4-carboxamide DIPEA (76 µl, 0.6 mmol) was added to a solution of 2'-methyl-5'-(5-methyl-1,3,4-oxadiazol-2-yl)-1,1'-biphenyl-4-carboxylic acid (59 mg, 0.2 mmol), 3-dimethylaminopropylamine (20 mg, 0.2 mmol), HBTU (91 mg, 0.24 mmol) and HOBT (27 mg, 0.2 mmol) in DMF (0.5 ml). The reaction was stirred at room temperature for 16 h. The DMF was evaporated under vacuum and the residue partitioned between DCM (5 ml) and water (5 ml). The organic phase was absorbed onto a silica flash column and eluted with DCM/ethanol/ammonia (80:8:1). The product fractions were concentrated under vacuum to give N-[(dimethylamino)propyl]-2'-methyl-5'-(5-methyl-1,3,4-oxadiazol-2-yl)-1,1'-biphenyl-4-carboxamide (37 mg, 49%).

NMR; $\delta H[^2H_6]$-DMSO 8.58, (1H, t), 7.93, (2H, d), 7.89, (1H, dd), 7.76, (1d), 7.54, (1H, d), 7.50, (2H, d), 3.30, (2H, m), 2.56, (3H, s), 2.31, (3H, s), 2.28, (2H, t), 2.14, (6H, s), 1.67, (2H, m). LCMS; retention time 2.25 min, MH$^+$ 379.

Example 4

N-(Cyclopropylmethyl)-2'-methyl-5'-(5-methyl-1,3,4-oxadiazol-2-yl)-1,1'-biphenyl-4-carboxamide a) Cyclopropylmethylamine (78 mg, 1.10 mmol), and 2'-methyl-5'-(5-methyl-1,3,4-oxadiazol-2-yl)-1,1'-biphenyl-4-carbonyl chloride (115 mg, 0.368 mmol) were mixed in DCM (15 ml) and stirred at room temperature for 17 h. The reaction was absorbed onto a silica flash column and eluted with DCM/ethanol/ammonia (150:8:1). The product fractions were concentrated under vacuum to give N-(cyclopropylmethyl)-2'-methyl-5'-(5-methyl-1,3,4-oxadiazol-2-yl)-1,1'-biphenyl-4-carboxamide as a white foam (75 mg, 59%).

NMR; $\delta H[^2H_6]$-DMSO 8.65, (1H, t), 7.95, (2H, d), 7.89, (1H, dd), 7.76, (1H, d), 7.55 –7.49, (3H, m), 3.17, (2H, t), 2.56, (3H, s), 2.31, (3H, s), 1.05, (1H, m), 0.43, (2H, m), 0.24, (2H, m). LCMS; retention times 3.15 min, MH$^+$348.

b) 2'-Methyl-5'-(5-methyl-1,3,4-oxadiazol-2-yl)-1,1'-biphenyl-4-carbonyl chloride Oxalyl chloride (0.073 ml, 0.82 mmol) was added to a suspension of 2'-methyl-5'-(5-methyl-1,3,4-oxadiazol-2-yl)-1,1'-biphenyl carboxylic acid (200 mg, 0.68 mmol), and DMF (2 drops) in DCM (10 ml) at 0° C. The reaction was stirred at room temperature for 1.5 h and the solvents evaporated under vacuum to give 2'-methyl-5'-(5-methyl-1,3,4 oxadiazol-2-yl)-1,1'-biphenyl-4-carbonyl chloride as a white solid (0.212 g, 100%).

NMR; $\delta H[^2H_6]$-DMSO 8.03, (2H, d), 7.90, (1H, dd), 7.76, (1H, d), 7.56–7.53, (3H, m), 2.56, (3H, s), 2.30, (3H, s).

Example 5

N-[3-(Diethylamino)propyl]-2'-methyl-5'-(5-methyl-1,3,4-oxadiazol-2-yl)-1,1'-biphenyl-4-carboxamide DIPEA (130 µl, 1.0 mmol) was added to a solution of 2'-methyl-5'-(5-methyl-1,3,4-oxadiazol-2-yl)-1,1'-biphenyl-4-carboxylic acid (100 mg, 0.34 mmol), 3-diethylaminopropylamine (49 mg, 0.37 mmol), HBTU (155 mg, 0.41 mmol) and HOBT (46 mg, 0.34 mmol) in DMF (1.0 ml). The reaction was stirred at room temperature for 66 h. The DMF was evaporated under vacuum and the residue partitioned between DCM (5 ml) and water (5 ml) The organic phase was absorbed onto a silica flash column and eluted with DCM/ethanol/ammonia (100:8:1). The product fractions were concentrated under vacuum to give N-[3-(diethylamino)propyl]-2'-methyl-5'-(5-methyl-1,3,4-oxadiazol-2-yl)-1,1'-biphenyl-4-carboxamide (88 mg, 64%).

NMR; $\delta H[^2H_6]$-DMSO 8.60, (1H, t), 7.92, (2H, d), 7.89, (1H, dd), 7.75, (1H, d), 7.54, (1H, d), 7.50, (2H, d), 3.30, (2H, m), 2.56, (3H, s), 2.46–2.41, (6H, m), 2.30, (3H, s), 1.65, (2H, m), 0.94, (6H, t). LCMS; retention time 2.44 min, MH$^+$ 407.

Example 6

N-(Cyclopropylmethyl)-N-methyl-2'-methyl-5'-(5-methyl-1,3,4-oxadiazol-2-yl)-1,1'-biphenyl-4-carboxamide N-(Cyclopropylmethyl)-N-methyl-2'-methyl-5'-(5-methyl-1,3,4-oxadiazol-2-yl)-1,1'-biphenyl-4-carboxamide was prepared from N-(cyclopropylmethyl)-2'-methyl-5'-(5-methyl-1,3,4-oxadiazol-2-yl)-1,1'-biphenyl-4-carboxamide and iodomethane using method H.

NMR; $\delta H[^2H_6]$-DMSO 7.89, (1H, dd), 7.76, (1H, d), 7.54, (1H, d), 7.47, (4H, s), 3.14–3.01, (5H, m), 2.56, (3H, s), 2.32, (3H, s), 1.08–0.95, (1H, b), 0.47, (2H, b), 0,29, (1H, b), 0.06, (1H, b). LCMS; retention time 3.20 min, MH$^+$ 362.

Example 7

N-(3-Hydroxypropyl)-N-methyl-2'-methyl-5'-(5-methyl-1,3,4-oxadiazol-2-yl)-1,1'-biphenyl-4-carboxamide N-(3-Hydroxypropyl)-N-methyl-2'-methyl-5'-(5-methyl-1,3,4-oxadiazol-2-yl)-1,1'-biphenyl-4-carboxamide was prepared from 2'-methyl-5'-(5-methyl-1,3,4-oxadiazol-2-yl)-1,1'-biphenyl-4-carboxylic acid and N-(3-hydroxypropyl)-N-methylamine using method I.

NMR; δH[$^2$H$_6$]-DMSO 7.89, (1H, d), 7.76, (1H, s), 7.54, (1H, d), 7.46, (4H, s), 4.51–4.42, (1H, m), 3.49, (2H, s), 3.32, (3H, s), 2.95, (2H, s), 2.56, (3H, s), 2.32, (3h, s), 1.75, (2H, m). LCMS; retention time 2.74 min, MH$^+$ 366.

Example 8

N-Cyclohexyl-N-ethyl-2'-methyl-5'-(5-methyl-1,34-oxadiazol-2-yl)-1,1'-biphenyl-4-carboxamide N-Cyclohexyl-N-ethyl-2'-methyl-5'-(5-methyl-1,3,4-oxadiazol-2-yl)-1,1'-biphenyl-4-carboxamide was prepared from 2'-methyl-5'-(5-methyl-1,3,4-oxadiazol-2-yl)-1,1'-biphenyl-4-carboxylic acid and N-cyclohexyl-N-ethylamine using method I.
NMR; δH[$^2$H$_6$]-DMSO 7.89, (1H, dd), 7.77, (1H, s), 7.54, (1H, d), 7.46, (2H, d), 7.41, (2H, d), 3.37, (2H, b), 3.22, (1H, b), 2.56, (3H, s), 2.31, (3H, s), 1.81–0.89, (13H, b). LCMS; retention time 3.57 min, MH$^+$ 404.

Example 9

N-Dicyclopropylmethyl-2'-methyl-5'-(5-methyl-1,3,4-oxadiazol-2-yl)-1,1'-biphenyl-4-carboxamide N-Dicyclopropylmethyl-2'-methyl-5'-(5-methyl-1,3,4-oxadiazol-2-yl)-1,1'-biphenyl-4-carboxamide was prepared from 2'-methyl-5'-(5-methyl-1,3,4-oxadiazol-2-yl)-1,1'-biphenyl-4-carboxylic acid and dicyclopropylmethylamine using method I.
NMR; δH[$^2$H$_6$]-DMSO 7.89, (1H, d), 7.77, (1H, d), 7.54, (1H, d), 7.46, (4H, m), 3.46, (2H, b), 3.22, (2H, b), 2.56, (3H, s), 2.32, (3H, s), 1.16, (1H, b), 0.98, (1H, b), 0.47, (4H, b), 0.33, (2H, b), 0.04, (2H, b). LCMS; retention time 3.59 min, MH$^+$ 402.

Example 10

2'-Methyl-N-methyl-5'-(5-methyl-1,3,4-oxadiazol-2-yl)-N-pentyl-1,1'-biphenyl-4-carboxamide 2'-Methyl-N-methyl-5'-(5-methyl-1,3,4-oxadiazol-2-yl)-N-pentyl-1,1'-biphenyl-4-carboxamide was prepared from 2'-methyl-5'-(S-methyl-1,3,4-oxadiazol-2-yl)-1,1'-biphenyl-4-carboxylic acid and methylpentylamine using method I.
NMR; δH[$^2$H$_6$]-DMSO 7.89, (1H, dd), 7.76, (1H, d), 7.54, (1H, d), 7.47, (4H, s), 3.45, (1H, m), 3.23, (1H, m), 2.96–2.93, (3H, m), 2.56, (3H, s), 2.31, (3H, s), 1.59–1.51, (2H, m), 1.32, (2H, b), 1.08, (2H, b), 0.90–0.77, (3H, m). LCMS; retention time 3.47 min, MH$^+$378.

Example 11

N-(Cyclopropylmethyl)-5'-(5-ethyl-1,3,4-oxadiazol-2-yl)-2'-methyl-1,1'-biphenyl-4-carboxamide a) N-(Cyclopropylmethyl)-5'-(hydrazinocarbonyl)-2'-methyl-1,1'-biphenyl-4-carboxamide (20 mg, 0.06 mmol) and triethylorthopropionate (211 mg, 1.2 mmol) were heated at 130° C. for 18 h. The excess triethylorthopropionate was evaporated under vacuum, the residue applied to a silica SPE and eluted with an ethyl acetate/cyclohexane gradient (1:8 to 1:0). The solvent was evaporated to yield N-(cyclopropylmethyl)-5'-(5-ethyl-1,3,4-oxadiazol-2-yl)-2'-methyl-1,1'-biphenyl-4-carboxamide (16.9 mg, 78%).
LCMS; retention time 3.36 min, MH$^+$ 362.

b) N-(Cyclopropylmethyl)-5'-(hydrazinocarbonyl)-2'-methyl-1,1'-biphenyl-4-carboxamide
5'-[2-t-Butoxycarbonyl(hydrazinocarbonyl)]-N-(cyclopropylmethyl)-2'-methyl-1,1'-biphenyl-4-carboxamide (450 mg, 1.06 mmol) was dissolved in trifluoroacetic acid (4 ml) and stirred at room temperature for 3.5 h. The trifluoroacetic acid was evaporated under vacuum and the residue was partitioned between DCM and aqueous sodium bicarbonate. The organic phase and any precipitate produced were separated, washed with brine and concentrated under vacuum to give N-(cyclopropylmethyl)-5'-(hydrazinocarbonyl)-2'-methyl-1,1'-biphenyl-4-carboxamide as a white solid (210 mg, 61%).
LCMS; retention time 2.79 min, MH$^+$ 324.

c) 5'-[2-t-Butoxycarbonyl(hydrazinocarbonyl)]-N-(cyclopropylmethyl)-2'-methyl-1,1'-biphenyl-4-carboxamide
4-[N-(Cyclopropylmethyl)aminocarbonyl]phenylboronic acid (356 mg, 1.63 mmol), t-butyl 2-(3-bromo-4-methylbenzoyl)hydrazine-1-carboxylate (537 mg, 1.63 mmol), tetrakis (triphenylphosphine)palladium (190 mg, 0.16 mmol) and aqueous sodium bicarbonate (1M, 2.5 ml) were heated in DME (5 ml) at 80° C. 9 h. The solvents were evaporated under vacuum and the residue purified on a silica flash column eluting with DCM/ethanol/ammonia (300:8:1) to give after evaporation of the solvent 5'-[2-t-butoxycarbonyl (hydrazinocarbonyl)]-N-(cyclopropylmethyl)-2'-methyl-1, 1'-biphenyl-4-carboxamide as a yellow foam (460 mg, 67%).
LCMS; retention time 3.28 min, MH$^+$ 424.

d) 4-[N-(Cyclopropylmethyl)aminocarbonyl]phenylboronic acid
(Cyclopropylmethyl)amine (470 mg, 6.0 mmol), 4-carboxyphenylboronic acid (1.0 g, 6.0 mmol), HOBT (810 mg, 6.0 mmol), HBTU (2.73 g, 7.2 mmol) and DIPEA (1.71 g, 7.2 mmol) were mixed in DMF (10 ml) and stirred at room temperature for 18 h. The DMF was evaporated under vacuum and the residue partitioned between DCM and aqueous sodium bicarbonate. The organic phase was separated, washed with water and brine and dried (magnesium sulphate). The solvent was evaporated under vacuum and the residue purified on a silica flash column eluting with DCM/ ethanol/ammonia (15:8:1 then 10:10:1), to give after evaporation of the solvents 4-[N-(cyclopropylmethyl)aminocarbonyl]phenylboronic acid (300 mg, 23%).
NMR; δH[$^2$H$_6$]-DMSO 8.54, (1H, t), 8.18, (2H, s), 7.83, (2H, d), 7.78, (2H, d), 3.15, (2H, m), 1.02, (1H, m), 0.42, (2H, m), 0.21, (2H, m).

Example 12

N-(Cyclopropylmethyl)-2'-methyl-5'-(5-n-propyl-1,3,3-oxadiazol-2-yl)-1,1'-biphenyl-4-carboxamide N-(Cyclopropylmethyl)-5'-(hydrazinocarbonyl)-2'-methyl-1,1'-biphenyl-4-carboxamide (20 mg, 0.06 mmol) and triethylorthobutarate (229 mg, 1.2 mmol) were heated at 130° C. for 18 h. The excess triethylorthobutarate was evaporated under vacuum, the residue applied to a silica SPE and eluted with an ethyl acetate/cyclohexane gradient (1:8 to 1:0). The solvent was evaporated to yield N-(cyclopropylmethyl)-2'-methyl-5'-(5-n-propyl-1,3,4-oxadiazol-2-yl)-1, 1'-biphenyl-4-carboxamide.
NMR; δH[$^2$H$_6$]-DMSO 8.64, (1H, t), 7.95, (2H, d), 7.90, (1H, dd), 7.76, (1H, d), 7.55, (1H, d), 7.50, (2H, d), 3.17, (2H, t), 2.89, (2H, t), 2.31, (3H, s), 1.77, (2H, m), 1.08, (1H, m), 0.96, (3H, t), 0.43, (2H, m), 0.24, (2H, m). LCMS; retention time 3.47 min, MH$^+$ 376.

Example 13

N-[2-(3,4-Dimethoxyphenylamino)-2-oxoethyl]-2'-methyl-5'-(5-methyl-1,3,4-oxadiazol-2-yl)-1,1'-biphenyl-4-carboxamide N-[2-(3,4-Dimethoxyphenylamino)-2-oxoethyl]-2'-methyl-5'-(5-methyl-1,3,4-oxadiazol-2-yl)-1,1'-biphenyl-4-carboxamide was prepared from 2'-methyl-5'-(5-methyl-1,3,4 oxadiazol-2-yl)-1,1'-biphenyl-4-carboxylic acid and 2-amino-N-(3,4-dimethoxyphenyl)acetamide using method I.

NMR; δH[$^2$H$_6$]-DMSO 9.93, (1H, s), 8.92, (1H, t), 8.01, (2H, d), 7.90, (1H, dd), 7.78, (1H, d), 7.56–7.53, (3H, m), 7.33, (1H, d), 7.10, (1H, dd), 6.89, (1H, d), 4.06, (2H, d), 3.71, (6H, m), 2.57, (3H, s), 2.32, (3H, s). LCMS; retention time 2.96 min, MH$^+$ 487.

Example 14

N-(3,3-Dimethylbutyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 3,3-dimethylbutylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(3,3-dimethylbutyl)-2'-methyl-5'-(5-methyl-1,3,4-oxadiazol-2-yl)-1,1'-biphenyl-4-carboxamide.

LCMS; retention time 3.46 min, MH$^+$ 378.

Example 15

N-(2,3-Dimethylcyclohexyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 2,3-dimethylcyclohexylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(2,3-dimethylcyclohexyl)-2'-methyl-5'-(5-methyl-1,3,4-oxadiazol-2-yl)-1,1'-biphenyl-4-carboxamide.

LCMS; retention time 3.57 min, MH$^+$ 404.

Example 16

N-(Isobutyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 Mg, 0.034 mmol), HOBT (6.0 mg, 0.044 mmol), 1-(3-dimethylaminopropyl)-3-ethyl carbodiimide hydrochloride (8.0 mg, 0.042 mmol) and isobutylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(isobutyl)-2'-methyl-5'-(5-methyl-1,3,4-oxadiazol-2-yl)-1,1'-biphenyl-4-carboxamide.

LCMS; retention time 3.21 min, MH$^+$ 350.

Example 17

N-[2,2-Dimethyl-1-(methylaminocarbonyl)propyl]-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 2-amino-N,3,3-trimethylbutanamide (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-[2,2-dimethyl-1-(methylaminocarbonyl)propyl]-2'-methyl-5'-(5-methyl-1,3,4-oxadiazol-2-yl)-1,1'-biphenyl-4-carboxamide.

LCMS; retention time 3.03 min, MH$^+$ 421.

Example 18

2'-Methyl-N-(3-methylcyclohexyl)-5'-(6-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 3-methylcyclohexylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give 2'-methyl-N-(3-methylcyclohexyl)-5'-(6-methyl-1,3,4-oxadiazol-2-yl)-1,1'-biphenyl-4-carboxamide.

LCMS; retention time 3.50 min, MH$^+$ 390.

Example 19

N-Cyclohexyl-2'-methyl-5'-(5-methyl-1,3,4-oxadiazol-2-yl)-1,1'-biphenyl carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and cyclohexylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-cyclohexyl-2'-methyl-5'-(5-methyl-1,3,4-oxadiazol-2-yl)-1,1'-biphenyl-4-carboxamide.

LCMS; retention time 3.38 min, MH+ 376.

Example 20

N-Cyclopropyl-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-arboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and cyclopropylamine (0.34 mmol) were mixed in DMF (0.7 ml) and the reaction left at room temperature for 18 hours. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-cyclopropyl-2'-methyl-5'-(5-methyl-1,3,4-oxadiazol-2-yl)-1,1'-biphenyl-4-carboxamide.

LCMS; retention time 3.25 min, MH+ 362.

Example 21

(1,2-Dimethylpropyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 1,2-dimethylpropylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(1,2-dimethylpropyl)-2'-methyl-5'-(5-methyl-1,3,4-oxadiazol-2-yl)-1,1'-biphenyl-4-carboxamide.

LCMS; retention time 3.31 min, MH+ 364.

Example 22

N-(1,3-Dimethylpentyl)-2'-methyl-5'-(5-methyl-1,3,4-oxadiazol-2-yl)-1,1'-biphenyl-4-carboxamide 2'-Methyl-5'-(5-methyl-1,3,1-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 1,3-dimethylpentylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(1,3-dimethylpentyl)-2'-methyl-5'-(5-methyl-1,3,4-oxadiazol-2-yl)-1,1'-biphenyl-4-carboxamide.

LCMS; retention time 3.58 min, MH+ 392.

Example 23

N-(2-Cyclohexylethyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl 4-carboxylic acid (11.3 mg, 0.034 mmol), HOBT (6.0 mg, 0.044 mmol), 1-(3 dimethylaminopropyl)-3-ethyl carbodiimide hydrochloride (8.0 mg, 0.042 mmol) and 2-cyclohexylethylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(2-cyclohexylethyl)-2'-methyl-5'-(5-methyl-1,3,4-oxadiazol-2-yl)-1,1'-biphenyl-4-carboxamide.

LCMS; retention time 3.69 min, MH+ 404.

Example 24

2'-Methyl-N-(2-methylbutyl)-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 2-methylbutylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give 2'-methyl-N-(2-methylbutyl)-5'-(5-methyl-1,3,4-oxadiazol-2-yl)-1,1'-biphenyl-4-carboxamide.

LCMS; retention time 3.33 min, MH+ 364.

Example 25

N-(Cyclobutyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and cyclobutylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(cyclobutyl)-2'-methyl-5'-(5-methyl-1,3,4-oxadiazol-2-yl)-1,1'-biphenyl-4-carboxamide.

LCMS; retention time 3.15 min, MH+ 348.

Example 26

N-(1-Cyclopropylethyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 1-cyclopropylethylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(1-cyclopropylethyl)-2'-methyl-5'-(5-methyl-1,3,4-oxadiazol-2-yl)-1,1'-biphenyl-4-carboxamide.

LCMS; retention time 3.13 min, MH+ 362.

Example 27

N-(2,4-Dimethyl-3-pentyl)-2'-methyl-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 2,4-dimethyl-3-pentylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give N-(2,4-dimethyl-3-pentyl)-2'-methyl-5'-(5-methyl-1,3,4-oxadiazol-2-yl)-1,1'-biphenyl-4-carboxamide.

LCMS; retention time 3.48 min, MH+ 392.

Example 28

2'-Methyl-N-(1-methylbutyl)-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 1-methylbutylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give 2'-methyl-N-(1-methylbutyl)-5'-(5-methyl-1,3,4-oxadiazol-2-yl)-1,1'-biphenyl-4-carboxamide.

LCMS; retention time 3.33 min, MH+ 364.

Example 29

2'-Methyl-N-(2-methylallyl)-5'-(5-methyl-1,3,4-oxadiazol-2-yl)-1,1'-biphenyl-4-carboxamide 2'-Methyl-5'-(5-methyl-1,3,4-oxadiazol-2-yl)-1,1'-biphenyl-4-carboxylic acid (11.3 mg, 0.034 mmol), HOBT (6.0 mg, 0.044 mmol), 1-(3-dimethylaminopropyl)-3-ethyl carbodiimide hydrochloride (8.0 mg, 0.042 mmol) and 2-methylallylamine (0.34 mmol) were mixed in DMF (0.7 ml) and the reaction left at room temperature for 18 h. The DMF was evaporated under vacuum and the residue partitioned between DCM (0.4 ml) and water (0.4 ml). The organic phase was washed with aqueous sodium hydroxide (0.5M, 0.2 ml) and the DCM evaporated under vacuum. The residue was purified by mass directed HPLC to give 2'-methyl-N-(2-methylallyl)-5'-(5-methyl-1,3,4-oxadiazol-2-yl)-1,1'-biphenyl-4-carboxamide.

LCMS; retention time 3.13 min, MH+ 348.

Abbreviations

DCM Dichloromethane
DIPEA N,N-Diisopropylethylamine
DME Dimethoxyethane
DMF Dimethylformamide
DMSO Dimethylsulphoxide
HATU O-(7-Azabenzotriazol-1-yl)-N,N,N',N'-tetramethyluronium hexafluorophosphate
HBTU O-Benzotriazol-1-yl-N,N,N',N'-tetramethyluronium hexafluorophosphate
HOBT 1-Hydroxybenzotriazole hydrate
PyBOP Benzotriazol-1-yl-oxy-tripyrrolidinophosphonium hexafluorophosphate
SPE Solid phase extraction
THF Tetrahydrofuran.

The activity of the compounds of the invention as p38 inhibitors may be demonstrated in the following assays:

p38 Kinase Assay

The peptide substrate used in the p38 assay was biotin-IPTSPITTTYFFFRRR-amide. The p38 and MEK6 proteins were purified to homogeneity from *E. coli* expression systems. The fusion proteins were tagged at the N-terminus with Glutathione-S-Transferase (GST). The maximum activation was achieved by incubating 20 uL of a reaction mixture of 30 nM MEK6 protein and 120 nM p38 protein in the presence of 1.5 uM peptide and 10 mM $Mg(CH_3CO_2)_2$ in 100 mM HEPES, pH 7.5, added to 15 uL of a mixture of 1.5 uM ATP with 0.08 uCi [g-P]ATP, with or without 15 uL of inhibitor in 6% DMSO. The controls were reactions in the presence (negative controls) or absence (positive controls) of 50 mM EDTA. Reactions were allowed to proceed for 60 min at room temperature and quenched with addition of 50 uL of 250 mM EDTA and mixed with 150 uL of Streptavidin SPA beads (Amersham) to 0.5 mg/reaction. The Dynatech Microfluor white U-bottom plates were sealed and the beads were allowed to settle overnight. The plates were counted in a Packard TopCount for 60 seconds. $IC_{50}$ values were obtained by fitting raw data to % I=100*(1−(I−C2)/(C1−C2)), where I was CPM of background, C1 was positive control, and C2 was negative control.

α P38 Fluorescence Polarisation Method

α P38 was prepared in house. SB4777790-R Ligand was diluted in HEPES containing $MgCl_2$, CHAPS, DTT and DMSO. This was added to blank wells of a Black NUNC 384 well plate. α P38 was added to this ligand mixture then added to the remainder of the 384 well plate containing controls and compounds. The plates were read on an LJL Analyst and Fluorescence Anisotropy used to calculate the compound inhibition.

The application of which this description and claims forms part may be used as a basis for priority in respect of any subsequent application. The claims of such subsequent application may be directed to any feature or combination of features described herein. They may take the form of product, composition, process or use claims and may include, by way of example and without limitation, one or more of the following claims:

The invention claimed is:

1. A compound of formula (I):

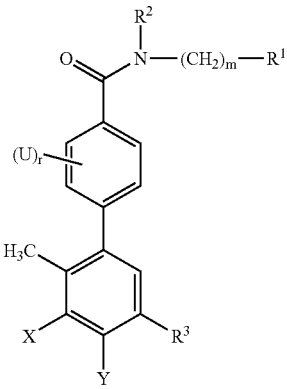

wherein
when m is 0 to 4, $R^1$ is selected from $C_{1-6}$alkyl, $C_{3-7}$cycloalkyl, $C_{2-6}$alkenyl, —$SO_2NR^4R^5$, —$CONR^4R^5$ and —$COOR^4$;
and when m is 2 to 4, $R^1$ is additionally selected from $C_{1-6}$alkoxy, hydroxy, $NR^4R^5$, —$NR^4SO_2R^5$, —$NR^4SOR^5$, —$NR^4COR^5$, and —$NR^4CONR^4R^5$;
$R^2$ is selected from hydrogen, $C_{1-6}$alkyl and —$(CH_2)_n$—$C_{3-7}$cycloalkyl;

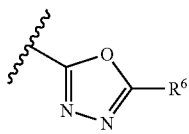

$R^4$ and $R^5$ are independently selected from hydrogen, $C_{1-6}$alkyl, heterocyclyl optionally substituted by $C_{1-4}$alkyl; and phenyl wherein the phenyl is optionally substituted by up to two groups independently selected from $C_{1-6}$alkoxy, $C_{1-6}$alkyl and halogen; or $R^4$ and $R^5$, together with the nitrogen atom to which they are bound, form a five- to six-membered heterocyclic or heteroaryl ring optionally containing one additional heteroatom selected from oxygen, sulfur and nitrogen, wherein the ring may be substituted by up to two $C_{1-6}$alkyl groups;
$R^6$ is selected from hydrogen and $C_{1-4}$alkyl;
U is selected from methyl and halogen;
X and Y are each selected independently from hydrogen, methyl and halogen;
m is selected from 0, 1, 2, 3 and 4 wherein each carbon atom of the resulting carbon chain may be optionally substituted with one or two groups selected independently from $C_{1-6}$alkyl;
n is selected from 0, 1, 2 and 3;
r is selected from 0, 1 and 2;
or a pharmaceutically acceptable salt or solvate thereof.

2. A compound according to claim 1 wherein $R^1$ is selected from $C_{1-4}$alkyl, $C_{3-6}$cycloalkyl, —$CONHCH_3$, —$SO_2NH_2$, —$SO_2N(CH_3)_2$, methoxy, —$NHSO_2CH_3$ and —$NHCOCH_3$.

3. A compound according to claim 1 wherein $R^1$ is selected from $C_{1-6}$alkyl, $C_{3-7}$cycloalkyl, $C_{2-6}$alkenyl, —$CONR^4R^5$, hydroxy and $NR^4R^5$.

4. A compound according to claim 1 wherein $R^2$ is selected from hydrogen, $C_{1-4}$alkyl and —$CH_2$-cyclopropyl.

5. A compound according to claim 4 wherein $R^2$ is hydrogen.

6. A compound according to claim 1 wherein $R^6$ is $C_{1-4}$alkyl.

7. A compound according to claim 1 wherein m is selected from 0, 1 and 2.

8. A process for preparing a compound as claimed in claim 1 which comprises:
reacting a compound of formula (XVI)

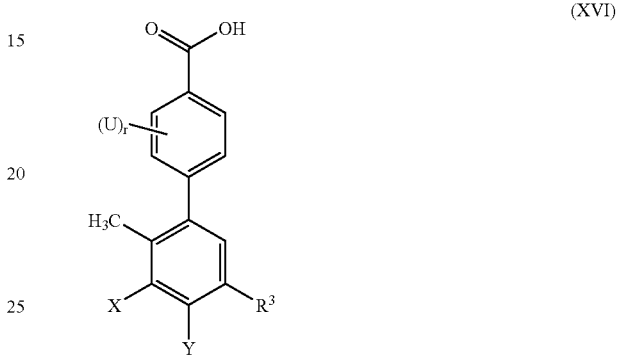

wherein $R^3$, U, X, Y and r are as defined in claim 1, with a compound of formula (XVII)

$R^1(CH_2)_mNH_2$      (XVII)

wherein $R^1$ and m are as defined in claim 1, under amide forming conditions, followed by reaction with a compound of formula (XVIII)

$R^2$-hal      (XVIII)

in which $R^2$ is as defined in claim 1 and hal is halogen, in the presence of a base.

9. A pharmaceutical composition comprising a compound according to claim 1 or a pharmaceutically acceptable salt or solvate thereof, in admixture with one or more pharmaceutically acceptable carriers, diluents or excipients.

10. A compound according to claim 1 which is:
N-(3-Hydroxypropyl)-2'-methyl-5'-(5-methyl-1,3,4-oxadiazol-2-yl)-1,1'-biphenyl-4-carboxamide;
N-(Cyclopropyl)-2'-methyl-5'-(5-methyl-,1,3,4-oxadiazol-2-yl)-1,1'-biphenyl-4-carboxamide;
N-[(Dimethylamino)propyl]-2'-methyl-5'-(5-methyl-1,3,4-oxadiazol-2-yl)-1,1'-biphenyl-4-carboxamide;
N-(Cyclopropyimethyl)-2'-methyl-5'-(5-methyl-1,3,4-oxadiazol-2-yl)-1,1'-biphenyl-4-carboxamide;
N-[3-(Diethylamino)propyl]-2'-methyl-5'-(5-methyl-1,3,4-oxadiazol-2-yl)-1,1'-biphenyl-4-carboxamide;
N-(Cyclopropylmethyl)-N-methyl-2'-methyl-5'-(5-methyl-1,3,4-oxadiazol-2-yl) -1,1'-biphenyl-4-carboxamide;
N-(3-Hydroxpropyl)-N-methyl-2'-methyl-5'-(5-methyl-1,3,4-oxadiazol-2-yl) -1,1'-biphenyl-4-carboxamide;
N-Cyclohexyl-N-ethyl-2'-methyl-5'-(5-methyl-1,3,4-oxadiazol-2-yl)-1,1'-biphenyl -4-carboxamide;
N-Dicyclopropylmethyl-2'-methyl-5'-(5-methyl-1,3,4-oxadiazol-2-yl)-1,1'-biphenyl-4-carboxamide;
2'-Methyl-N-methyl-5'-(5-methyl-1,3,4-oxadiazol-2-yl)-N-pentyl-1,1'-biphenyl-4-carboxamide;
N-(Cyclopropylmethyl)-5'-(5-ethyl-1,3,4-oxadiazol-2-yl)-2'-methyl-1,1'-biphenyl -4-carboxamide;

N-(Cyclopropylmethyl)-2'-methyl-5'-(5-n-propyl-1,3,4-oxadiazol-2-yl)-1,1'-biphenyl-4-carboxamide;

N-[2-(3,4-Dimethoxyphenylamino)-2-oxoethyl]-2'-methyl-5'-(5-methyl-1,3,4-oxadiazol-2-yl)-1,1'-biphenyl-4-carboxamide;

N-(3,3-Dimethylbutyl)-2'-methyl-5'-(5-methyl-1,3,4-oxadiazol-2-yl)-1,1'-biphenyl-4-carboxamide;

N-(2,3-Dimethylcyclohexyl)-2'-methyl-5'-(5-methyl-1,3,4-oxadiazol-2-yl)-1,1'-biphenyl-4-carboxamide;

N-(Isobutyl)-2'-methyl-5'-(5-methyl-1,3,4-oxadiazol-2-yl)-1,1'-biphenyl-4-carboxamide;

N-[2,2-Dimethyl-1-(methylaminocarbonyl)propyl]-2'-methyl-5'-(5-methyl-1,3,4-oxadiazol-2-yl)-1,1'-biphenyl-4-carboxamide;

2'-Methyl-N-(3-methylcyclohexyl)-5'-(5-methyl-1,3,4-oxadiazol-2-yl)-1,1'-biphenyl-4-carboxamide;

N-Cyclohexyl-2'-methyl-5'-(5-methyl-1,3,4-oxadiazol-2-yl)-1,1'-biphenyl-4-carboxamide;

N-Cyclopropyl-2'-methyl-5'-(5-methyl-1,3,4-oxadiazol-2-yl)-1,1'-biphenyl-4-carboxamide;

(1,2-Dimethylpropyl)-2'-methyl-5'-(5-methyl-1,3,4-oxadiazol-2-yl)-1,1'-biphenyl-4-carboxamide;

N-(1,3-Dimethylpentyl)-2'-methyl-5'-(5-methyl-1,3,4-oxadiazol-2-yl)-1,1'-biphenyl-4-carboxamide;

N-(2-Cyclohexylethyl)-2'-methyl-5'-(5-methyl-,1,3,4-oxadiazol-2-yl)-1,1'-biphenyl-4-carboxamide;

2'-Methyl-N-(2-methylbutyl)-5'-(5-methyl-1,3,4-oxadiazol-2-yl)-1,1'-biphenyl-4-carboxamide;

N-(Cyclobutyl)-2'-methyl-5'-(5-methyl-1,3,4-oxadiazol-2-yl)-1,1'-biphenyl-4-carboxamide;

N-(1-Cyclopropylethyl)-2'-methyl-5'-(5-methyl-1,3,4-oxadiazol-2-yl)-1,1'-biphenyl-4-carboxamide;

N-(2,4-Dimethyl-3-pentyl)-2'-methyl-5'-(5-methyl-1,3,4-oxadiazol-2-yl)-1,1'-biphenyl-4-carboxamide;

2'-Methyl-N-(1-methylbutyl)-5'-(5-methyl-1,3,4-oxadiazol-2-yl)-1,1'-biphenyl-4-carboxamide; or and 2'-Methyl-N-(2-methylallyl)-5'-(5-methyl-1,3,4-oxadiazol-2-yl)-1,1'-biphenyl-4-carboxamide; or a pharmaceutically acceptable salt or solvate thereof.

11. A compound according to claim 6 wherein $R^6$ is methyl.

12. A compound according to claim 1 wherein $R^6$ is methyl; $R^2$ is hydrogen or methyl, X and Y are hydrogen, and r is 0.

13. A compound according to claim 12 wherein $R^1$ is hydroxy, cyclopropyl, dimethylamine, diethylamine, or $CONR^4R^5$.

14. A pharmaceutical composition comprising a compound according to claim 10 or a pharmaceutically acceptable salt or solvate thereof, in admixture with one or more pharmaceutically acceptable carriers, diluents or excipients.

* * * * *